(12) United States Patent
Yanuma et al.

(10) Patent No.: US 9,451,936 B2
(45) Date of Patent: Sep. 27, 2016

(54) ENDOSCOPIC SURGICAL TOOL

(75) Inventors: Yutaka Yanuma, Tokyo (JP); Takashi Nagata, Tokyo (JP); Tsukasa Kobayashi, Tokyo (JP); Isao Sasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1193 days.

(21) Appl. No.: 11/775,568

(22) Filed: Jul. 10, 2007

(65) Prior Publication Data

US 2009/0018469 A1 Jan. 15, 2009

(51) Int. Cl.
| | |
|---|---|
| *A61B 10/04* | (2006.01) |
| *A61B 17/221* | (2006.01) |
| *A61B 17/00* | (2006.01) |
| *A61B 10/02* | (2006.01) |
| *A61B 17/22* | (2006.01) |
| *A61B 17/29* | (2006.01) |

(52) U.S. Cl.
CPC ............ *A61B 10/04* (2013.01); *A61B 17/221* (2013.01); *A61B 17/00234* (2013.01); *A61B 2010/0216* (2013.01); *A61B 2017/22039* (2013.01); *A61B 2017/2929* (2013.01); *A61B 2090/031* (2016.02); *A61B 2090/037* (2016.02)

(58) Field of Classification Search
CPC ................ A61B 2019/301; A61B 2019/307; A61B 10/04; A61B 17/00234; A61B 2017/2929
USPC ....... 600/300, 562, 563, 569, 572, 573, 581, 600/582, 101, 104, 127, 129, 131, 137, 153, 600/156
See application file for complete search history.

(56) References Cited

U.S. PATENT DOCUMENTS

| | | | |
|---|---|---|---|
| 4,653,510 A * | 3/1987 | Koll .............................. 600/569 |
| 5,352,197 A | 10/1994 | Hammersmark et al. |
| 6,454,717 B1 | 9/2002 | Pantages et al. |
| 2004/0260201 A1 | 12/2004 | Mueller, Jr. |
| 2007/0123928 A1* | 5/2007 | Farnan ......................... 606/200 |
| 2008/0033239 A1* | 2/2008 | Kogiso ................ A61B 17/122 600/106 |
| 2008/0077046 A1* | 3/2008 | Burg .................. A61B 10/0291 600/569 |
| 2009/0270877 A1* | 10/2009 | Johnson et al. .............. 606/108 |
| 2011/0021950 A1* | 1/2011 | Daniels .................. A61B 10/02 600/569 |

FOREIGN PATENT DOCUMENTS

| | | |
|---|---|---|
| JP | S62-133926 A | 6/1987 |
| JP | 05-000142 | 1/1993 |

(Continued)

OTHER PUBLICATIONS

Notice of Allowance dated Dec. 4, 2012 from corresponding Japanese Patent Application No. 2008-167348, together with an English language translation.

*Primary Examiner* — Adam J Eiseman
(74) *Attorney, Agent, or Firm* — Scully, Scott, Murphy & Presser, P.C.

(57) ABSTRACT

The present invention is related to an endoscopic treatment tool which is inserted to a body cavity endoscopically including a wire, a surgical section which is disposed on a first end of the wire and used for treatment inside the body cavity, and an operator section which is disposed on the second end of the wire and moves in conjunction with the wire so as to rotate by a rotary operation; and the movement of the operator section in conjunction with the wire is released upon exerting more than a predetermined torsional load on the wire.

14 Claims, 13 Drawing Sheets

(56) References Cited

FOREIGN PATENT DOCUMENTS

| | | |
|---|---|---|
| JP | 9-524 A | 1/1997 |
| JP | 11-276491 A | 10/1999 |
| JP | 2001-258830 A | 9/2001 |
| JP | 2001-269349 | 10/2001 |
| JP | 2002-253562 | 9/2002 |
| JP | 2004-781 A | 1/2004 |
| JP | 2007-152098 A | 6/2007 |
| WO | WO 2006/100882 A1 | 9/2006 |

* cited by examiner

ENDOSCOPIC SURGICAL TOOL

BACKGROUND OF THE INVENTION

1. Field of the Invention

The present invention relates to endoscopic surgical tools which are endoscopically inserted into a body.

2. Description of the Related Art

Endoscopic treatment tools such as a biopsy brush provided with synthetic fibers inserted between a stranded wire have been used conventionally in order to sample tissue from a body which is used for medical tests. When tissue is sampled with the biopsy brush above, tissue is often sampled by rotating the brush section with a rotary operation of a handle disposed at a proximal end of a wire.

However, tissue sampling target sites such as a bile duct have several narrow portions and a friction often exerts between tissue walls and the brush. If the rotary operation above is performed in this case, the wire that rotates though the brush section does not rotate due to the friction, so there is a possibility of breaking the wire upon exerting an excessive torsional load.

SUMMARY OF THE INVENTION

The present invention was conceived in view of the above-described circumstances and has as its objective the provision of an endoscopic surgical tool which can be operated safely even when a torsional load is exerted on a wire.

An endoscopic surgical tool according to a first aspect of the present invention is an endoscopic surgical tool which is inserted into a body endoscopically: the tool includes a wire, a surgical section disposed at a first end of the wire which is used for treatment in the body, an operation section disposed at a second end of the wire which moves in conjunction with the wire so as to rotate by a rotary operation; and the movement of the operating section in conjunction with the wire is released upon exerting more than a predetermined excessive torsional load on the wire.

The endoscopic surgical tool according to the present invention may further include a brittle section which is disposed in the operation section side of the wire and breaks with a smallest torsional load which may exerts on the wire, and the brittle section may break upon exerting more than the predetermined torsional load on the wire.

The operator section may include a first operating member in which the second end of the wire is fixed and a second operating member which is fixed to the first end of the wire.

The operator section may include a first operating member in which the second end of the wire is fixed; and a second operating member which is bonded by an adhesive on the first operating member; and the adhesion between the first operating member and the second operating member may be detached upon exerting more than the predetermined torsional load on the wire.

The operator section may include a first operating member in which the second end of the wire is fixed and a second operating member which is fixed on the first operating member; and the first operating member may include a strain relief portion provided with notches formed along the periphery direction intermittently, the strain relief portion may be ruptured upon exerting more than the predetermined torsional load on the wire.

The endoscopic surgical tool according to a second aspect of the present invention is an endoscopic surgical tool which is inserted into a body endoscopically: the tool includes a wire, a surgical section which is disposed on the first end of the wire and used for treatment in a body, a first operating member in which the second end of the wire is fixed, and a second operating member which is fixed at the first operating member and moves in conjunction with the wire so as to rotate by a rotary operation; and the movement of the second operating member in conjunction with the wire is released upon exerting more than a predetermined torsional load on the wire.

The endoscopic surgical tool according to the present invention may further include a holding member which is disposed between the first and second operating members and holds the first and second operating members by friction.

The endoscopic surgical tool according to the present invention may further include: a first engaging member which is disposed on the first operating member, and a second engaging member which is disposed on the second operating member which fixes the second operating member to the first operating member by engaging the first engaging member; and the engagement between the first and second engaging members may be released upon exerting more than the predetermined torsional load.

The first operating member may be a tube which includes a notch on its outer surface and the second end of the wire is inserted through the first operating member and exposed to the outside of the first operating member from the notch. In this case, when more than a second predetermined torsional load which is smaller than the predetermined torsional load is exerted to the wire, the second end portion may start to be drawn into the first operating member; and when more than the predetermined torsional load is exerted on the wire, the second end portion may be completely housed in the first operating member so as to stop the movement of the second operating member in conjunction with the wire.

DETAILED DESCRIPTION OF THE INVENTION

The first embodiment of the present invention of the endoscopic treatment tool will be explained with reference to FIGS. 1 to 3.

Figure 1:
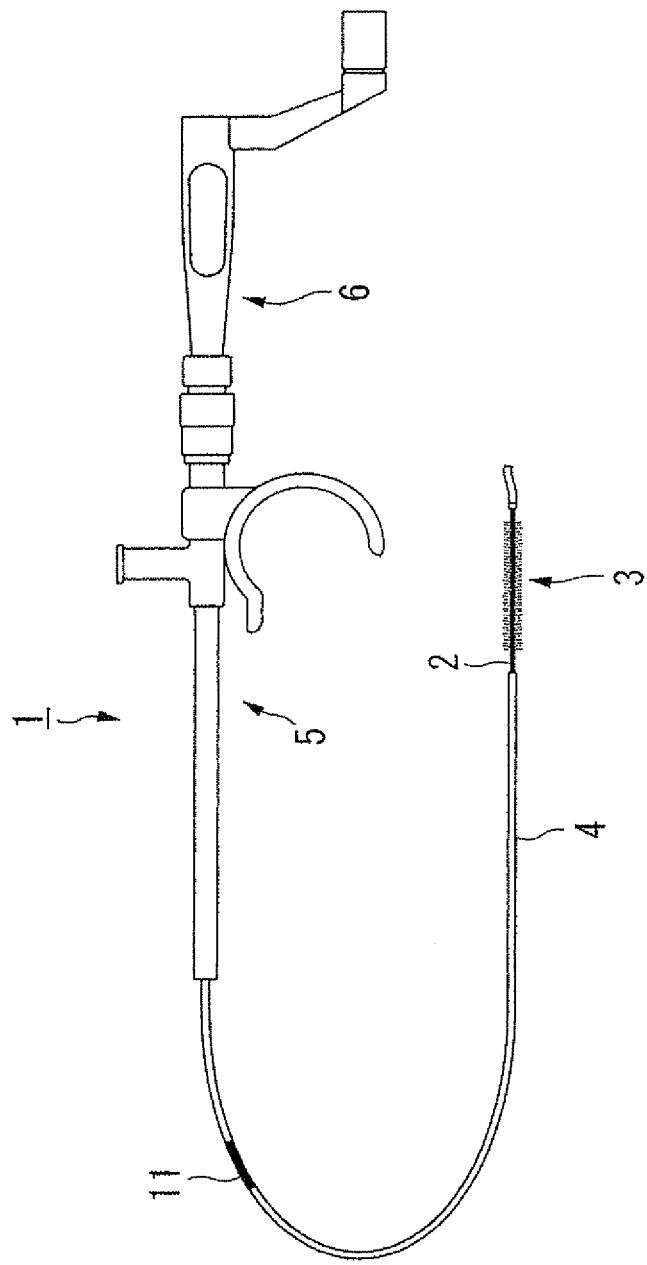
FIG. 1 shows the endoscopic treatment tool according to a first embodiment of the present invention.

FIG. 1 is an overall structure of an endoscopic treatment tool 1 of the present embodiment. As shown in FIG. 1, the endoscopic treatment tool 1 includes a wire 2, a surgical section 3 disposed at a distal end of the wire 2, a sheath 4 in which the wire 2 is inserted through, a main body 5 in which the sheath 4 is fixed and an operator section 6 which is disposed at a proximal side of the main body 5.

Figure 2:
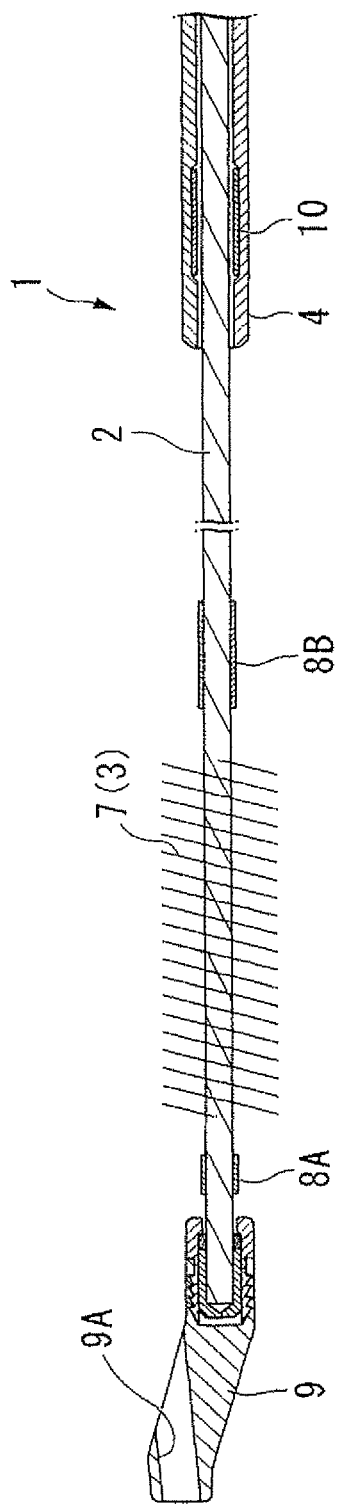
FIG. 2 is an enlarged cross-sectional view of the distal portion of the endoscopic treatment tool.

FIG. 2 is an enlarged diagram in the vicinity of the distal end of the wire 2 (a first end portion). The wire 2 is formed by twisting two metal wires together. A plurality of synthetic fibers 7 is inserted in the metal wires at the distal end portions of the wire 2 so as to form a brush-shaped surgical section 3.

Brush markers 8A and 8B made of stainless steel are disposed at both the front and rear portions of the surgical section 3 by caulking, respectively, so that the markers become guides to understand the position of the surgical section 3 when the endoscopic treatment tool 1 is operated under fluoroscopy.

An edge chip 9 is disposed at the front portion of the surgical section 3 so as to freely rotate relative to the wire 2. A through hole 9A where a guide wire which is described later is inserted is disposed at the edge chip 9.

The sheath 4 is a flexible tube formed of, for example, synthetic resin and a pipe-like index member 10 formed of stainless steel is fixed inside of and near the distal end thereof as shown in FIG. 2. The index member 10 becomes as a marker to understand a position of the distal end of the sheath when the endoscopic treatment tool 1 is operated under fluoroscopy.

The brush markers 8A, 8B or the index member 10 may be formed of materials such as tantalum which has a high level of visibility under fluoroscopy, instead of stainless steel.

Furthermore, a colored section 11 is disposed at a predetermined position of the main body 5 side of the sheath 4 as shown in FIG. 1 so that the colored section 11 becomes as a guide to determine the positional relationship of the sheath and the endoscope when the sheath is inserted into the endoscope as described later.

Figure 3:
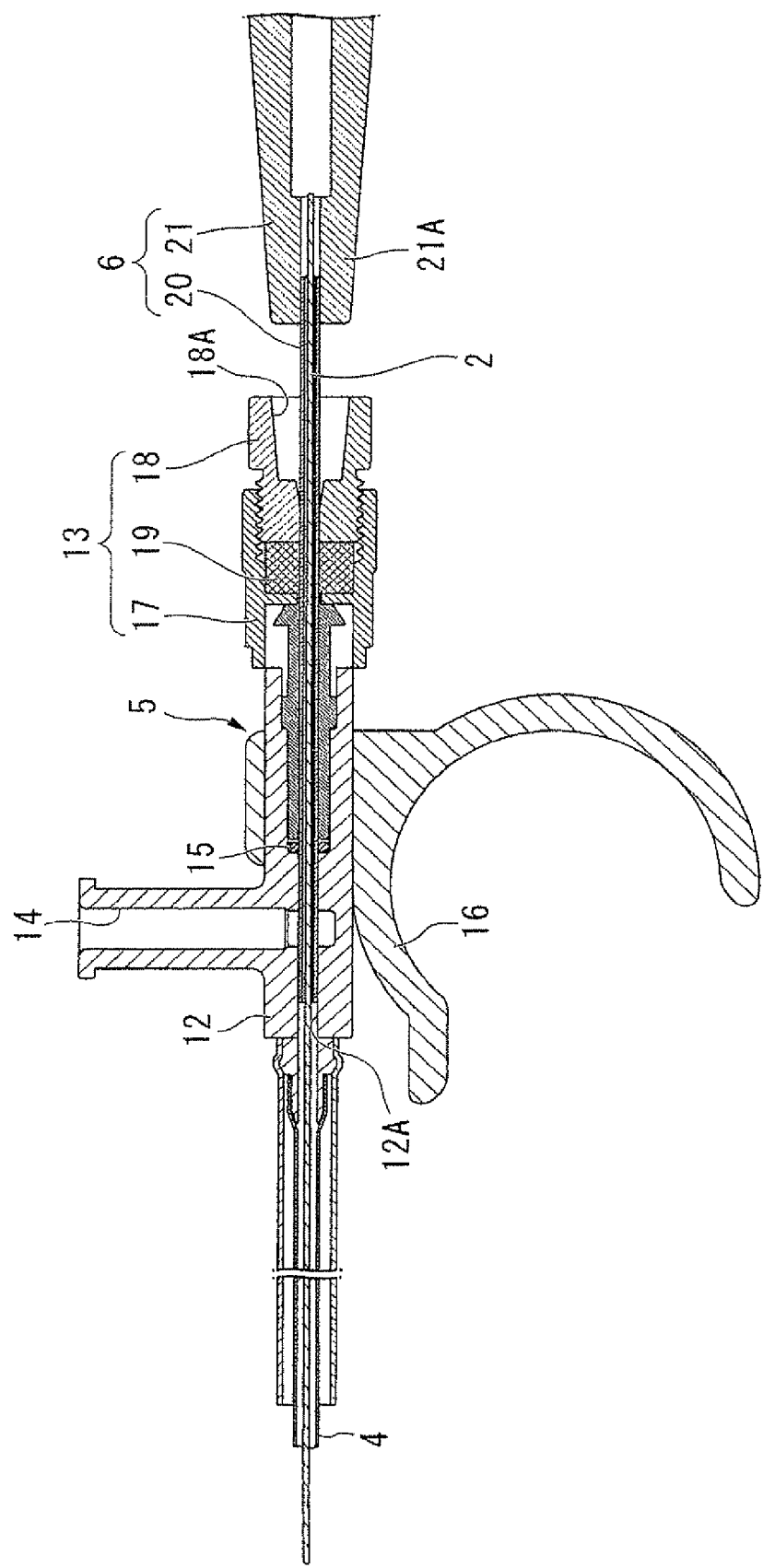
FIG. 3 is a cross-sectional view showing the main body and in the vicinity of the endoscopic treatment tool.

FIG. 3 is a cross-sectional view of the main body 5. The main body includes a main body member 12 and the connecting section 13 disposed at a rear end of the main body member 12. The main body member 12 is a substantially pipe-like member made of, for example, synthetic resin and a through hole 12A where the wire 2 is inserted is formed along a central axial line.

The sheath 4 is fixed by press-fitting at a distal end of the main body member 12. An inlet 14 for a contrast agent to be filled is disposed at the upper portion of the main body 5. The inlet 14 joins the through hole 12A as shown in FIG. 3. A rubber O-ring 15 is disposed at a pre-determined position of a rear side of the inlet 14 of the through hole 12A so as to maintain water-tightness in order to prevent leakage of the contrast agent filled in the inlet 14 to the rear end of the main body. Furthermore, a substantially C-shaped anchor 16 is disposed at a lower portion of the main body member 12 so that an endoscopic treatment tool 1 can be anchored on an endoscope during a procedure.

A connecting section 13 includes a connector 17 which is disposed at a rear end of the main body member 12, a fitting member 18 where the operator section 6 is engaged and a packing 19 disposed between the connector 17 and the fitting member 18. A through hole is provided in each member included in the connecting section 13 along their central axis.

The fitting member 18 is screw-fitted to an inside of the substantial pipe-like connecting member 17 so that it is structured to allow a movement within a predetermined area in an axial direction. A through hole 18A of the fitting member 18 is formed in a tapered shape in which the diameter increases gradually as it approaches a rear end so that it is structured to allow engagement of the operator section 6 as described later. The packing 19 is formed of elastic materials such as rubber.

Figure 4:
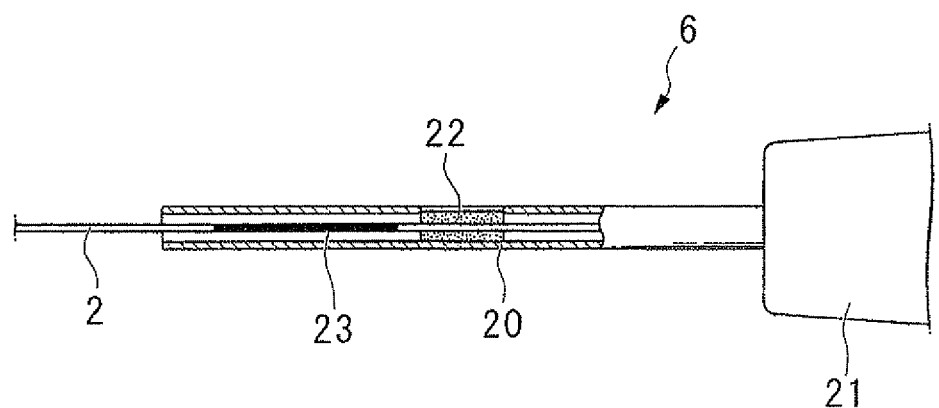
FIG. 4 is an enlarged view that includes a cross-section through a portion of the operating section of the endoscopic treatment tool.

FIG. 4 is an enlarged view that includes a cross-section through a portion of the operator section 6. The operator section 6 includes a pipe 20 (a first operating member) where the wire 2 is inserted and a handle 21 (a second operating member) which is fixed to the pipe 20.

The pipe 20 is formed of metal and an inserted rear end of the wire 2 (the second end portion) is fixed to the pipe 20 by brazing a filler metal 22 drained into the pipe 20. A proximal end of the pipe 20 is fixed to the handle 21 by welding.

The handle 21 is made of, for example, synthetic resin. By performing a rotary operation with the handle 21 around the axial line, the pipe 20 and the wire 2 integrated into the handle 21 move in conjunction with the handle 21 so as to rotate around the axial line.

The operator section 6 configured as above is inserted into the main body 5 as shown in FIG. 3, and the pipe 20 and the wire 2 fixed to the pipe 20 can slide inside a through hole of the main body 5 along an axial direction. An end portion 21A on the pipe 20 side of the handle 21 is formed in a tapered shape, that is fitted into the through hole 18A of the fitting member 18 shown in FIG. 3 so that it is structured by allowing a positional identification of the surgical section 3.

Furthermore, as shown in FIG. 4, a brittle portion 23 is disposed in the vicinity of the rear end of the wire 2. The strength of the brittle portion is reduced by tempering so as to break before other portions of the wire 2 when a torsional load is exerted on the wire 2 by a rotary operation with the handle 21.

The movement of the endoscopic treatment tool 1 when in use configured as above is described with reference to FIG. 5. Note that descriptions below are when intrabiliary tissue is sampled by using the endoscopic treatment tool 1.

First, an endoscope 100 is inserted into a body cavity of a patient with a conventional procedure. A distal end of the endoscope 100 is advanced in the vicinity of a duodenal papilla R1, and then a guide wire (not shown) is inserted into an instrument channel from a forceps port 101 of the endoscope 100.

The guide wire which is protruded from the distal end of the endoscope 100 is advanced into a bile duct R2 from the duodenal papilla R1 and detained under fluoroscopy. Next, the sheath 4 is advanced along the guide wire by inserting the rear end of the guide wire into the through hole 9A of the edge chip 9 and inserting it into the forceps port 101, at a position where the surgical section 3 of the endoscopic treatment tool 1 is housed in the sheath 4. For a smooth operation, the main body 5 is fixed to the endoscope 100 by the anchor 16 if necessary.

Figure 5:
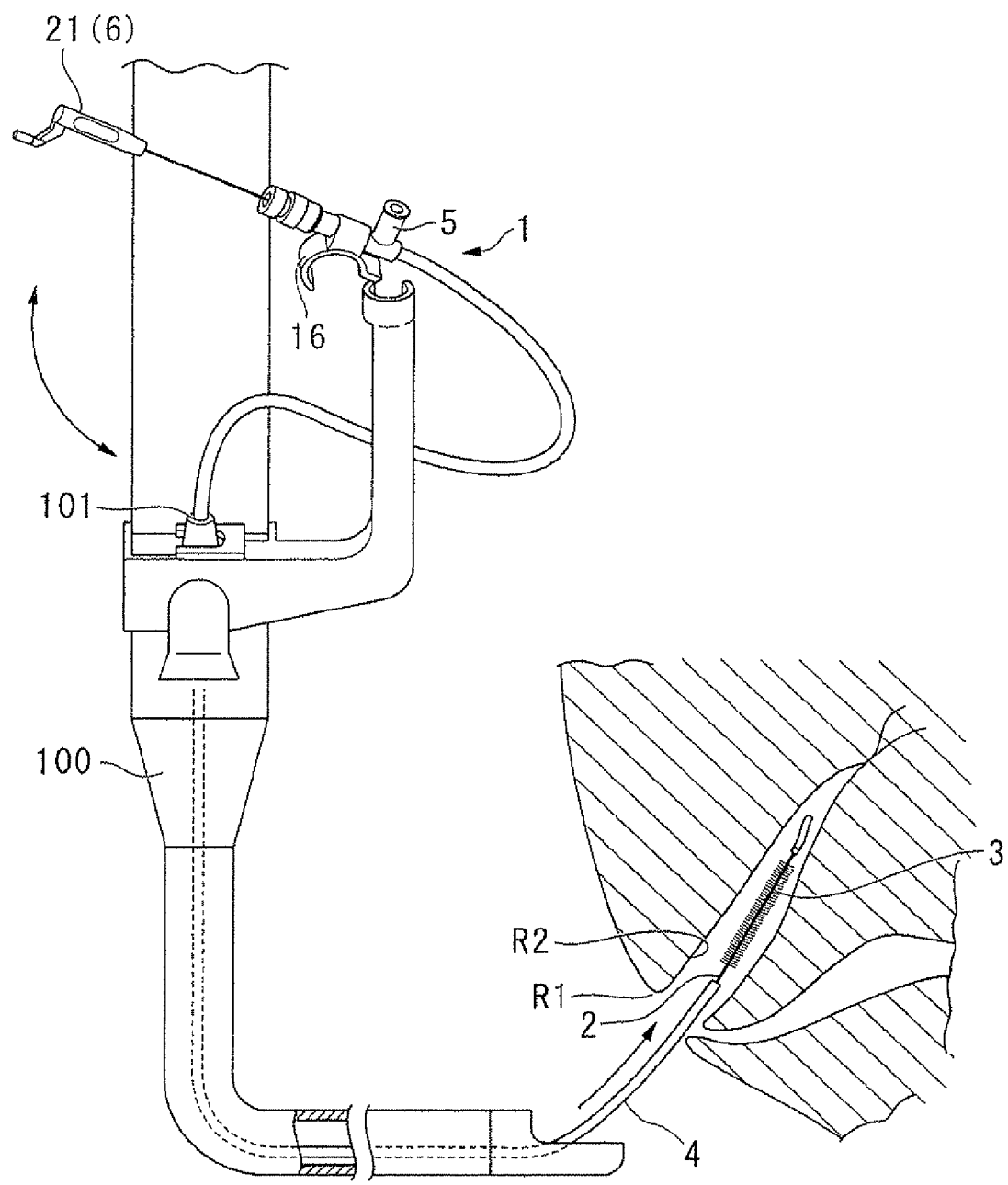
FIG. 5 shows the movement of the endoscopic treatment tool when in use.

As shown in FIG. 5, tissue is sampled by protruding the surgical section 3 from the sheath 4 and the surgical section 3 is advanced and retracted, or rotated via the operator section 6 after the surgical section 3 of the endoscopic treatment tool 1 is advanced into the bile duct 12.

When the wire 2 is fixed with respect to the sheath 4, extension and retraction of the wire 2 is controlled by advancing the handle 21 and the end portion 21A is fitted into the through hole 18A of the connecting section 13. When the wire 2 is fixed at a position where the wire 2 is further advanced with respect to the sheath 4, the fitting member 18 is screwed into the connector 17 so that the packing 19 is pressed by the fitting member 18, and deflects toward the through hole disposed on the packing 19. Therefore, extension and retraction of the wire 2 is controlled by the pipe 20 being sandwiched by the packing 19.

When tissue is harvested at a narrow cavity area such as intrahepatic bile duct, the surgical section 3 may become difficult to rotate due to friction between the surgical section 3 and an inner surface of, for example, a bile duct. At this time, if the handle 21 continues to be rotated, there may be a possibility of breaking the wire 2 by exerting an excessive torsional load than the predetermined amount.

According to the endoscopic treatment tool 1 of the present embodiment, a user can safely manipulate an extension and retraction movement and removal of the endoscopic treatment tool 1 by holding the wire 2 protruded from the rear portion of the main body 5 in case the wire 2 is broken, since the wire 2 is broken at a brittle portion 23 which has a least strength so as to release the movement of the wire 2 in conjunction to the operator section 6.

Furthermore, since the edge chip 9 where the guide wire is inserted is fitted so as to freely rotate with respect to the wire 2, the wire 2 can be smoothly operated without being twisted even the guide wire is meandered or twisted.

In the preceding embodiment, the brittle portion 23 is disposed by tempering. However, the method for forming the brittle portion is not limited thereto; it is also acceptable to provide the brittle section by other methods.

Figure 6:
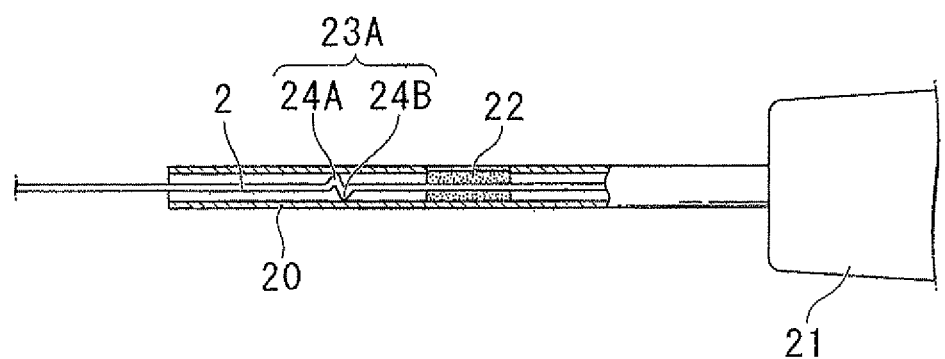
FIG. 6 is an enlarged view that includes a cross-section through a portion of an example of modification of the operating section of the endoscopic treatment tool.
Figure 7:
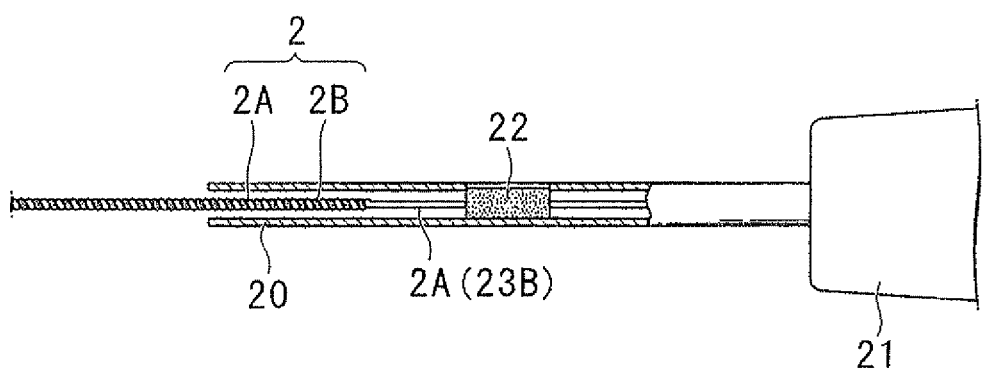
FIG. 7 is an enlarged view that includes a cross-section through a portion of an example of modification of the operating section of the endoscopic treatment tool.

For example, as shown in an example of a modification in FIG. 6, the brittle portion 23A may be formed by providing a folding portion 24A and 24B in the vicinity of the rear end of the wire 2 so that the brittle portion 23A is more likely to be broken in comparison to other members. Furthermore, as shown in an example of modification in FIG. 7, the brittle portion 23B may be formed by terminating a strand of an element wire 2A and 2B comprised of the wire 2 in the vicinity of the rear end and only the element wire 2A is brazed.

Furthermore, in the above embodiment, the example in which the operator section includes the pipe 20 and the handle 21, and the wire 2 is fixed to the pipe 20 is described. However the structure of the present application is not limited thereto, for instance it is also acceptable if the operator section 6 does not include the pipe 20 and the rear end of the wire 2 is directly fixed to the handle 21.

Furthermore, predetermined amounts of torsional load in which the brittle portion 23 breaks can be adjusted freely by controlling the manufacturing method of the brittle portion 23. For example, when the wire 2 of the surgical section 3 is tempered in order to increase the fixability of fiber 7 at the surgical section 3, the brittle portion 23 can be manufactured in the way that the brittle portion 23 becomes more brittle than the surgical section 3 by increasing the degree of tempering the brittle portion 23. In this way, breaking the surgical section 3 by torsional load before the brittle portion 23 can be prevented so as to obtain the same effect of the present invention in the above embodiment.

The second embodiment of the present invention of the endoscopic treatment tool will be explained with reference to FIGS. 8 and 9. An endoscopic treatment tool 31 of the present embodiment differs from the endoscopic treatment tool 1 described above by means of releasing the movement of the operator section in conjunction with the wire due to the manufacturing process of the operator section, not the wire as in the first embodiment, when an excessive torsional load is exerted.

In the following description, components that are the same as the first embodiment shall be provided with the same numeric symbol and redundant descriptions shall be omitted.

Figure 8:
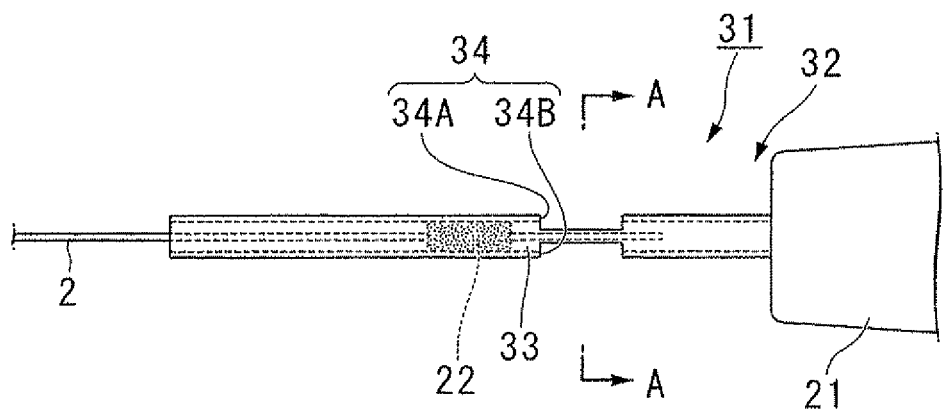
FIG. 8 is an enlarged view of the endoscopic treatment tool according to a second embodiment of the present invention.

FIG. 8 is an enlarged cross-sectional diagram of an operator section 32 of the endoscopic treatment tool 31. The operator section 32 includes the handle 21 aid the pipe 33. A notch 34A and 34B are formed along the periphery direction intermittently at the upper and lower portion of the pipe 33, and a strain relief portion 34 is formed. The wire 2 and the pipe 33 are fixed to each other by brazing at a more distally positioned area than the strain relief portion 34.

Figure 9:
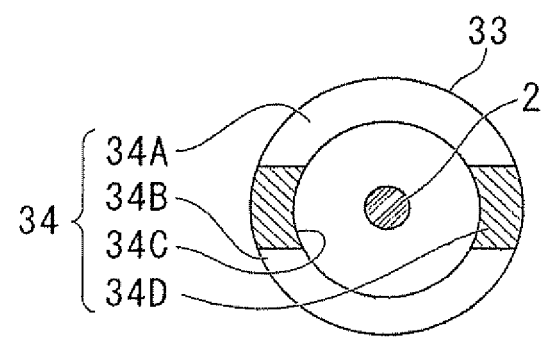
FIG. 9 is a cross-sectional view taken along line A-A shown in FIG. 8.

FIG. 9 is a cross-sectional view as seen from the line A-A in FIG. 8. The strain relief portion 34 is more easily broken compared to other members of the pipe 33 since members of the pipe 33 are only disposed at two places on side walls 34C and 34D as shown in FIG. 9. When the strain relief portion 34 is disposed, the size of the notches 34A and 34B is adjusted so as to rupture the strain relief portion 34 with less torsional load than that of the wire 2. The number of notches is not limited to 2, but the number may be one or more than three.

According to an endoscopic treatment tool 31 of the present embodiment, when the surgical section 3 looses its rotatability due to a friction force against the tissues around, for example, a biliary duct and an excessive torsional load is exerted by a rotary operation of the handle 21, the strain relief portion 34 of the pipe 33 is broken by cutting. Then the movement of the wire 2 in conjunction with the operator section 6 is released hence the torsional load exerted to the wire 2 is absorbed so that breakage of the wire 2 can be prevented.

The present embodiment describes an example of releasing the movement of the wire 2 in conjunction with the operator section 6 by providing the strain relief portion at the pipe 33, however the manufacturing method of the operator section 6 in order to release the movement of the wire 2 in conjunction with the operator section 6 when an excessive torsional load is exerted on the wire 2 is not limited thereto.

For instance, the pipe 33 and the handle 21 may be bonded by, for example, an adhesive without being fixed by welding.

In this case, the amount and strength of an adhesive may be adjusted so as to detach the bonding between the pipe 33 and the handle 21 in order to release the movement of the operator section 6 in conjunction with the wire 2 when excessive torsional load is exerted on the wire 2.

Next, a third embodiment of the present invention will be explained with reference to FIGS. 10 and 11. The endoscopic treatment tool 41 of the present embodiment differs from the endoscopic treatment tool 1 described above in that a pipe of an operator section and a handle are held by friction force.

In the following description, components that are the same as the first embodiment shall be provided with the same numeric symbols and redundant descriptions shall be omitted.

Figure 10:
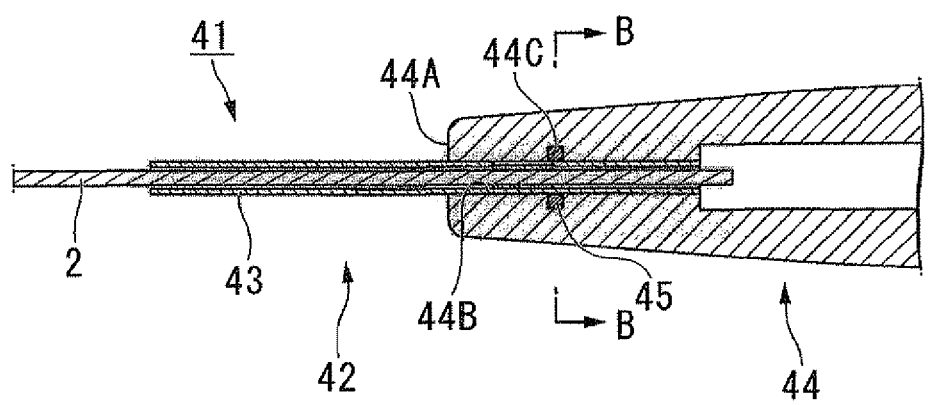
FIG. 10 is an enlarged cross-sectional view of the endoscopic treatment tool according to a third embodiment of the present invention.
Figure 11:
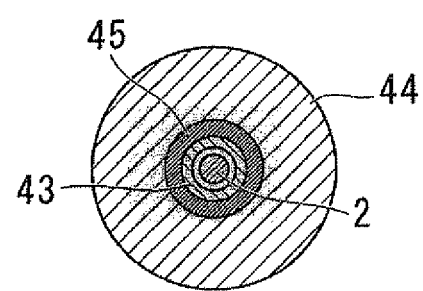
FIG. 11 is a cross-sectional view taken along line B-B shown in FIG. 10.

FIG. 10 is an enlarged cross-sectional diagram of an operator section 42 of the endoscopic treatment tool 41. As shown in FIG. 10, the pipe 43 is inserted into an insertion hole 44B disposed at an end portion 44A of a handle 44, the insertion hole 44B has substantially the same inside diameter as an outside diameter of the pipe 43.

A ring-shaped groove 44C is disposed along a periphery direction at a predetermined position of the insertion hole 44B. A holding member 45 such as an O-ring made of an elastic material such as rubber is disposed inside of the groove 44C. FIG. 11 is a cross-sectional view seen from the line B-B in FIG. 10. As shown in FIG. 11, an outer periphery plane of the pipe 43 is in contact with the holding member 45, and the pipe 43 and the handle 44 are integrated by a friction force generated by the holding member 45. The above holding by the friction force generated by the holding member 45 can be adjusted so as to release with a less torsional load than a load which has a possibility of breaking the wire.

When a handle 44 of the endoscopic treatment tool 41 is rotary operated, the handle 44, the pipe 43 and the wire 2 move in conjunction with each other and rotate with the friction force of the holding member 45 so as to rotate the surgical section 3 disposed at the edge of the wire 2, at a normal state where there is no friction between the surgical section 3 and tissue in the vicinity thereof.

When the surgical section 3 looses the ability to rotate such as by entering into a narrow cavity, a torsional load is exerted by a rotary operation of the handle 44. When an excessive torsional load is applied, the handle 44 rotates free by releasing the movement of the pipe 43 due to the friction of the holding member 45 so that an excessive torsional load will not be applied to the wire 2. Hence the wire 2 is prevented from being damaged.

According to the endoscopic treatment tool 41 of the present embodiment, the movement of the sheath 4 in conjunction with the wire 2 is released by releasing the friction generated by the holding member 45 which holds the pipe 43 and the handle 44. Since breakage of the wire 2 can be prevented without damaging the wire 2 or the operator section 42, an andoscopic treatment tool which is safely operated continuously even when an excessive torsional load is transiently exerted on the wire 2.

Next, a forth embodiment of an endoscopic treatment tool 51 of the present invention will be explained with reference to FIGS. 12 and 13. The endoscopic treatment tool 51 of the present embodiment differs from the endoscopic treatment tool 1 of the first embodiment by means of movement of a handle at an operator section in conjunction with a pipe.

In the following description, components that are the same as the first embodiment shall be provided with the same numeric symbols and redundant descriptions shall be omitted.

Figure 12:
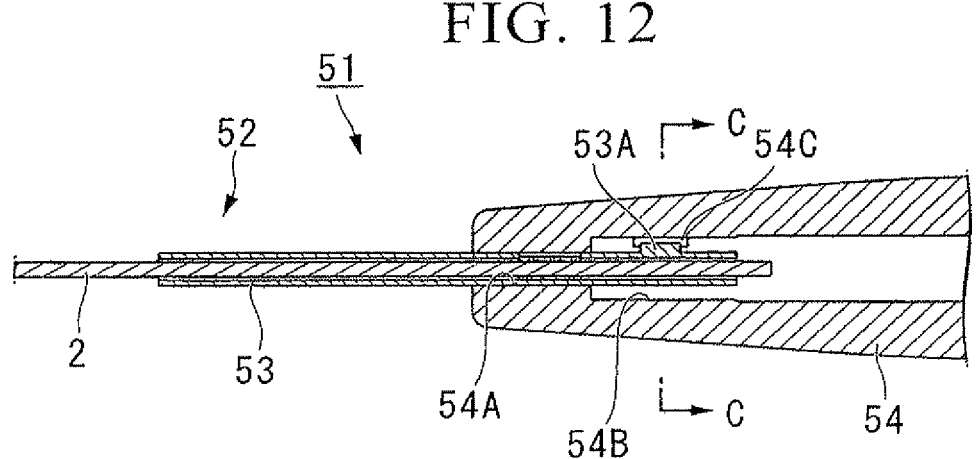
FIG. 12 is an enlarged cross-sectional view of the endoscopic treatment tool according to a forth embodiment of the present invention.

FIG. 12 is an enlarged diagram of an operator section 52 of the endoscopic treatment tool 51. An insertion hole of a handle 54 where a pipe 53 is inserted consists of a first half portion 54A of the pipe 53 side and a second half portion 54B with a larger diameter than the first half portion 54A located proximally to an operator.

Figure 13:
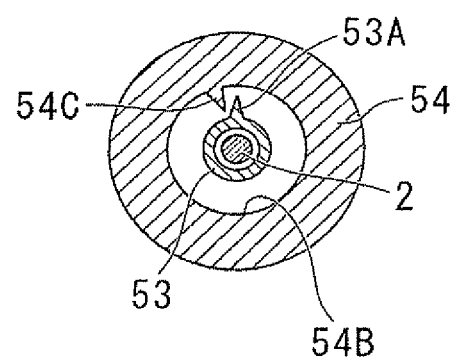
FIG. 13 is a cross-sectional view taken along line C-C shown in FIG. 12.

FIG. 13 is a cross-sectional view as seen from the line C-C in FIG. 12. As shown in FIG. 13, a first engaging member 53A is disposed on an outer surface of the pipe 53 by protruding toward the outside of the diameter direction. A second engaging member 54C is disposed on an inner surface of the second half portion 54B of the handle 54 by protruding toward the inside of the diameter direction so as to engage the first engaging member 53A.

When the handle 54 of the endoscopic treatment tool 51 is rotated, the second engaging member 54C of the handle and the first engaging member 53A of the pipe 53 are engaged so that the pipe 53 and the wire 2 fixed on the pipe 53 are rotated in conjunction with the handle 54.

When the surgical section 3 looses its rotatability by, for example, entering into a narrow cavity, a torsional load is exerted by the rotary operation of the handle 54. When an excessive torsional load is exerted, the movement of the handle 54 in conjunction with the pipe 53 is released by rotating the second engaging member 54C over the first engaging member 53A. Consequently, the handle 54 freely rotates so as to release the torsional load exerted on the wire 2. Thus a breakage of the wire 2 can be prevented.

According to the endoscopic treatment tool 51 of the present embodiment, the breakage of the wire can be prevented without damaging the wire and operator section as per the endoscopic treatment tool 41 described above. Furthermore, a torsional load exerted on the wire 2 is easily released by releasing the movement of the handle 54 in conjunction with the pipe 53, hence an endoscopic treatment tool which can be operated more safely can be constructed.

According to the present embodiment, the example of the structure where both the first engaging member 53A and the second engaging member 54C are protruded is described, however the structure is not limited thereto, instead, one of them may be grooved so as to engage the first engaging member 53A and the second engaging member 54C.

Next, a fifth embodiment of the present invention is described with reference to FIGS. 14 to 16C. An endoscopic treatment tool 61 of the present embodiment differs from the endoscopic treatment tool 1 described above in that a rear end of a wire is protruded outside of a pipe.

In the following description, components that are the same as the first embodiment shall be provided with the same numeric symbols and redundant descriptions shall be omitted.

Figure 14:
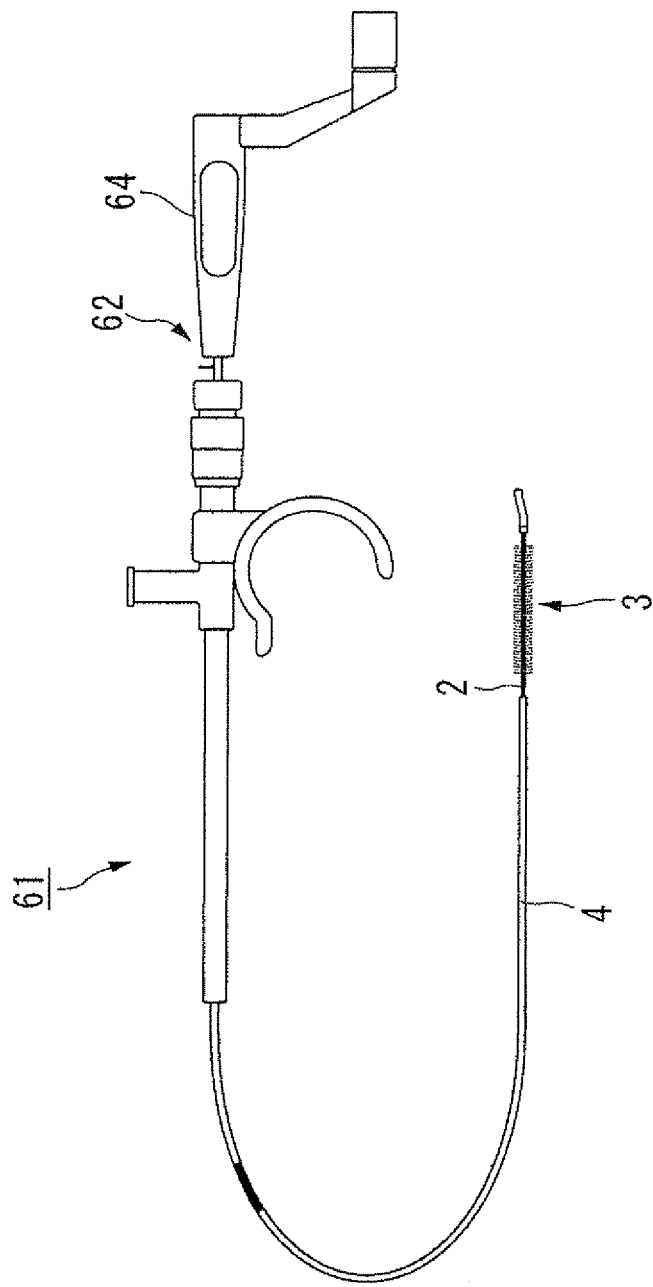
FIG. 14 shows the endoscopic treatment tool according to a fifth embodiment of the present invention.

FIG. 14 is an overall view of the endoscopic treatment tool 61. In the endoscopic treatment tool 61, the rear end of the wire 2 is protruded from an operator section 62.

Figure 15:
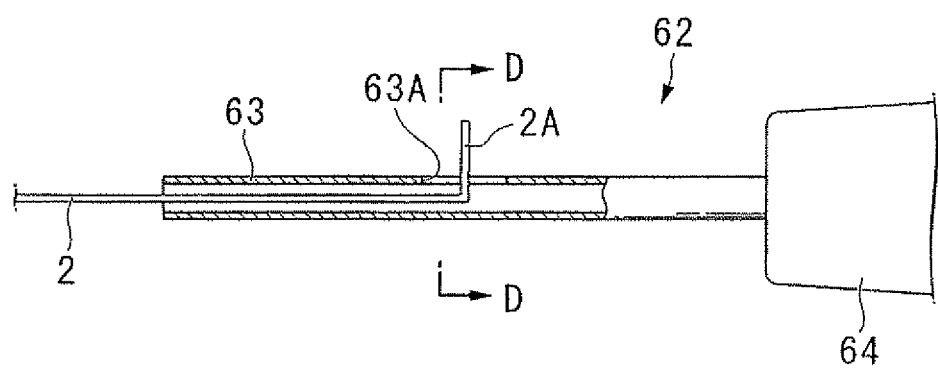
FIG. 15 is an enlarged view that includes a cross-section through a portion of the operating section of endoscopic treatment tool.

FIG. 15 is an enlarged view that includes a cross-section of the operator section 62. A pipe 63 is fixed on a handle 64 by welding. A notch 63A is disposed at a predetermined position on the outer surface of the pipe 63, and the rear end 2A of the wire 2 is protruded out to the pipe 63 from the notch 63A by being bent substantially 90 degrees.

A movement of an endoscopic treatment tool 61 when in use is described. First, the surgical section 3 housed inside of the sheath 4 is made to advance into the bile duct R2 by the same procedure as shown in FIG. 5.

Figure 16A:
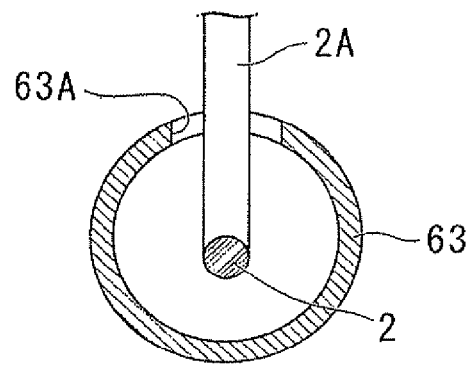
FIG. 16A is a cross-sectional view taken along line D-D shown in FIG. 15.
Figure 16B:
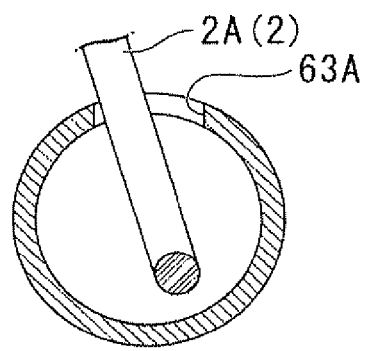
FIG. 16B is a cross-sectional view taken along line D-D shown in FIG. 15.
Figure 16C:
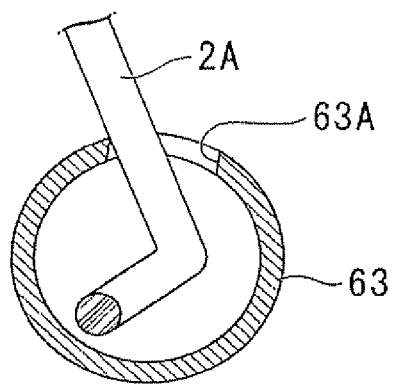
FIG. 16C is a cross-sectional view taken along line D-D shown in FIG. 15.

FIGS. 16A to 16C are cross-sectional views as seen from the line D-D in FIG. 15. The notch 63A of the pipe 63 integrated with a handle 64 and the rear end 2A of the wire 2 are not in contact at a normal status as shown in FIG. 16A. When the handle 64 is rotated, the operator section 62 moves in conjunction with the wire 2 so as to rotate the surgical section 3 by contacting the notch 63A and the rear end 2A of the wire 2 as shown in FIG. 16B.

When the surgical section 3 looses its rotatability due to being in a narrow cavity and so on, more than a predetermined value (the second predetermined value) of torsional load is exerted to the wire 2, the rear end 2A of the wire 2 stats to be drawn into the pipe 63 by bending the rear end 2A of the wire 2 as shown in FIG. 16C. Furthermore, when a larger torsional load than the second predetermined value is exerted on the wire 2 by a continuous rotary operation of the handle 64, the rear end 2A is completely drawn into the pipe 63. Consequently, the wire 2 is no longer engaged with the pipe 63 so that the wire 2 does not move in conjunction with the operator section 62. Thus exertion of more than the predetermined torsional load on the wire 2 can be prevented.

According to the endoscopic treatment tool 61 of the present embodiment, even when the rear end 2A of the wire 2 is contained in the pipe 63, a repeated rotary operation is possible by protruding the rear end 2A from the notch 63A by rotating the handle 64 in an opposite direction. Therefore, the breakage of the wire can be prevented without damaging the wire and the operator section as per the endoscopic treatment tools 41 and 51 described above.

While preferred embodiments of the invention have been described and illustrated above, it should be understood that these are exemplary of the invention and are not to be considered as limiting. Additions, omissions, substitutions, and other modifications can be made without departing from the spirit or scope of the invention.

Figure 17:
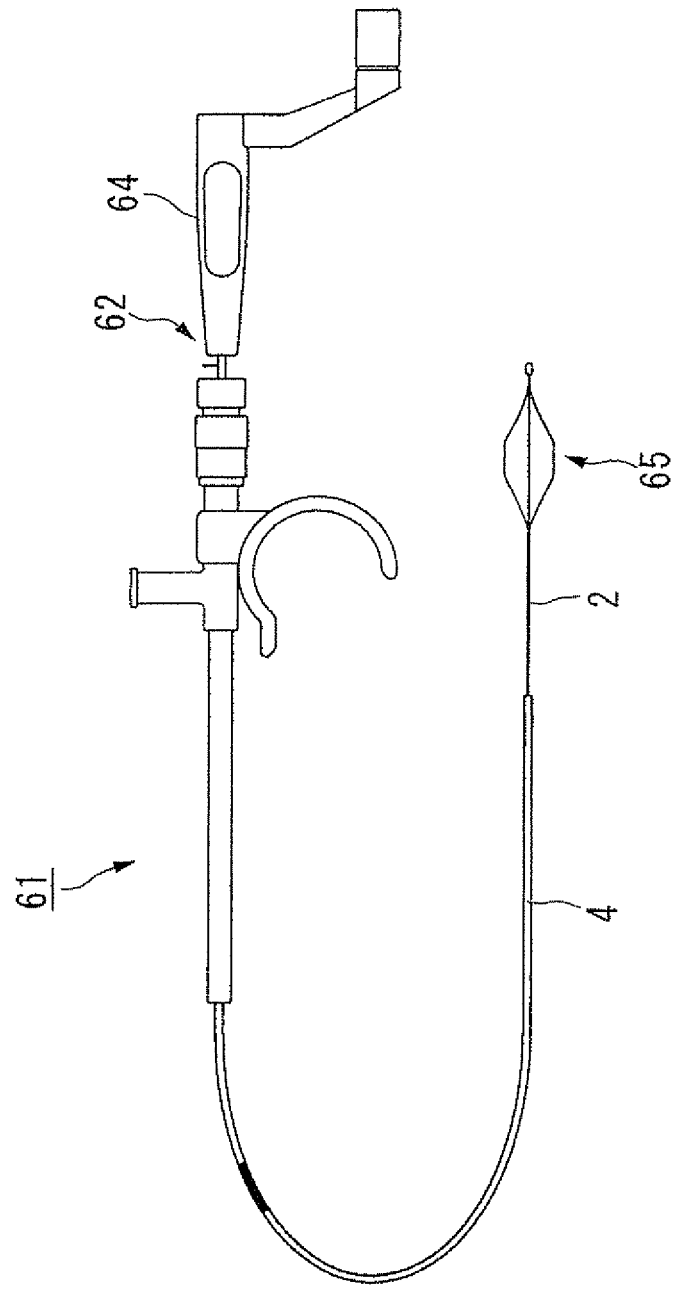
FIG. 17 shows an example of a modification to the endoscopic treatment tool in the fifth embodiment.

For instance, in the embodiment above, the surgical tools in which the distal end of the surgical section is a brush are given as examples; the invention is not limited thereto. For instance, the surgical section may be a conventionally known basket 65 which is formed by twisting a plurality of wires as an example of a modification shown in FIG. 17. Apart from the embodiments above, the present invention can also be applied in any endoscopic treatment tools in which the surgical section is rotated.

Furthermore, the target tissue and organs are not limited in the bile duct as described above; the present invention can be applied in any organ even where rotation of the surgical section may be difficult.

Accordingly, the invention is not to be considered as being limited by the foregoing description, and is only limited by the scope of the appended claims.

What is claimed is:

1. An endoscopic surgical tool which is inserted into a body endoscopically, the endoscopic surgical tool comprising:
    an endoscope that has a channel, the channel extending from a proximal end to a distal end along a longitudinal direction of the endoscope, the endoscope being configured to observe from the distal end;
    a wire having flexibility, the wire being configured to be inserted into the channel from an opening disposed at the proximal end, the wire having a first end configured to protrude from the distal end and a second end configured to protrude from the opening to outside of the body;
    a surgical section disposed on the first end of the wire, the surgical section being configured to perform treatment on living tissue in the body;
    a handle fixed to the second end of the wire, the second end of the wire protruding from the opening to the outside of the body, the handle being configured to operate the wire and to be rotated around the longitudinal direction; and
    a brittle section disposed on the wire between the handle and the opening, the brittle section being configured to, when a torsional load that is applied on the wire and causes the wire to rotate around the longitudinal direction is less than or equal to a predetermined torsional load, rotate the wire depending on rotation of the handle in the same direction as the handle rotating, and when the torsional load applied on the wire is greater than the predetermined torsional load, prevent the rotation of the handle from being transmitted to the wire.

2. The endoscopic surgical tool according to claim 1, wherein the handle includes a first operating member in which the second end of the wire is fixed and a second operating member which is fixed to the first operating member.

3. The endoscopic surgical tool according to claim 1, wherein the handle includes a first operating member in which the second end of the wire is fixed and a second operating member which is bonded by an adhesive on the first operating member and the adhesion between the first operating member and the second operating member is detached upon exerting more than the predetermined torsional load.

4. The endoscopic surgical tool according to claim 1, wherein
    the handle includes a first operating member in which the second end of the wire is fixed and a second operating member which is fixed to the first operating member; and
    the brittle section includes a strain relief portion in the first operation member and the strain relief portion is provided with notches formed along a periphery direction intermittently at an upper and lower portion, the strain relief portion being broken upon exerting more than the predetermined torsional load.

5. The endoscopic surgical tool according to claim 1, wherein the brittle section is made of the same material as that of the wire and is tempered.

6. The endoscopic surgical tool according to claim 1, wherein the brittle section is made of the same material as that of the wire and is provided with folding portions in a proximal end portion of the wire.

7. The endoscopic surgical tool according to claim 1, wherein the brittle section is formed by terminating a strand of a plurality of element wires comprised of the wire in a proximal end portion of the wire and only one of the plurality of element wires is brazed.

8. The endoscopic surgical tool according to claim 1, wherein
    the handle is configured to rotate the wire and the surgical section around an axis of the wire by the handle being rotated, and
    the brittle section is configured to prevent a first torsional load from being transmitted from the handle to the wire when a second torsional load, which is different from the first torsional load and acts on the wire during the handle rotating the surgical section, exceeds the predetermined torsional load.

9. An endoscopic surgical tool which is inserted into a body using an endoscope that has a channel therein, the channel extending from a proximal end to a distal end along a longitudinal direction of the endoscope, the endoscope being configured to observe from the distal end, the endoscopic surgical tool comprising:
- a wire having flexibility, the wire being configured to be inserted into the channel from an opening disposed at the proximal end, the wire having a first end configured to protrude from the distal end and a second end configured to protrude from the opening to outside of the body;
- a surgical section which is disposed on the first end of the wire, the surgical section being configured to perform treatment on living tissue in the body;
- a first operating member formed in a pipe shape, the first operating member being fixed to the second end of the wire inside the first operating member, the first operating member being further configured to be rotated around the longitudinal direction, the second end of the wire protruding from the opening to the outside of the body;
- a second operating member fixed to the first operating member, the second operating member being configured to operate the first operating member, the first operating member and the wire being configured to rotate depending on rotation of the second operating member; and
- a brittle section disposed on the wire between the second operating member and the opening and inside the first operating member, the brittle section being configured to, when a torsional load that is applied on the wire and causes the wire to rotate around the longitudinal direction is less than or equal to a predetermined torsional load, rotate the wire depending on the rotation of the second operating member in the same direction as the second operating member rotating, and when the torsional load applied on the wire is greater than the predetermined torsional load, prevent the rotation of the second operating member from being transmitted to the wire.

10. An endoscopic surgical tool according to claim 9, further including a holding member which is disposed between the first and second operating members and holds the first and second operating members by friction.

11. The endoscopic surgical tool according to claim 9, further comprising:
- a first engaging member which is disposed on the first operating member; and
- a second engaging member which is disposed on the second operating member and fixes the second operating member to the first operating member by engaging the first engaging member; wherein
- the brittle section includes a releasing portion for releasing the engagement between the first and second engaging members upon exerting more than the predetermined torsional load.

12. The endoscopic surgical tool according to claim 9, wherein
- the brittle section includes the first operating member being a tube which includes a notch on an outer surface of the tube and the second end of the wire is inserted through the first operating member and exposed to outside of the first operating member from the notch; wherein
- when more than a second predetermined torsional load which is smaller than the predetermined torsional load is exerted on the wire, the second end of the wire starts to be drawn into the first operating member; and
- when more than the predetermined torsional load is exerted on the wire, the second end of the wire is completely drawn into the first operating member so as to stop the movement of the second operating member in conjunction with the wire.

13. The endoscopic surgical tool according to claim 9, wherein
- the second end of the wire is disposed to be inserted into the first operating member,
- inside the first operating member, the second end of the wire is brazed to the first operating member along the longitudinal direction with a filler metal, and
- the brittle section is disposed between a portion where the filler metal is provided and a distal end of the first operating member.

14. An endoscopic surgical tool which is inserted into a body, the endoscopic surgical tool comprising:
- a wire having a first end configured to be inserted into the body and a second end configured to be arranged outside the body in a state in which the first end is inserted into the body and advanced within the body;
- a surgical section which is disposed on the first end of the wire and used for treatment in the body;
- a first operating member fixed to the second end of the wire and arranged outside the body;
- a second operating member which is fixed at the first operating member, the second operating member being provided with a handle such that rotation of the handle rotates the second operating member around an axis, which in turn rotates the first operating member and the wire fixed thereto; and
- a portion which does not transmit a torsional load from the second operating member to the wire when the torsional load is greater than a predetermined torsional load, the portion being disposed inside of the first operating member; wherein
- the portion comprises the first operating member being a tube which includes a notch on its outer surface and the second end of the wire is inserted through the first operating member and exposed to outside of the first operating member from the notch; wherein
- when more than a second predetermined torsional load which is smaller than the predetermined torsional load is exerted on the wire, the second end of the wire starts to be drawn into the first operating member; and
- when more than the predetermined torsional load is exerted on the wire, the second end of the wire is completely drawn into the first operating member so as to stop the movement of the second operating member in conjunction with the wire.

\* \* \* \* \*